US006854346B2

United States Patent
Nimberger

(10) Patent No.: US 6,854,346 B2
(45) Date of Patent: Feb. 15, 2005

(54) PURGING SYSTEM FOR USE WITH A GAS SAMPLING SYSTEM

(75) Inventor: Spencer M. Nimberger, Houston, TX (US)

(73) Assignee: PGI International, Ltd., Houston, TX (US)

(*) Notice: Subject to any disclaimer, the term of this patent is extended or adjusted under 35 U.S.C. 154(b) by 0 days.

(21) Appl. No.: 10/244,869

(22) Filed: Sep. 17, 2002

(65) Prior Publication Data

US 2003/0051565 A1 Mar. 20, 2003

Related U.S. Application Data

(60) Provisional application No. 60/323,128, filed on Sep. 17, 2001.

(51) Int. Cl.[7] ................................................. G01N 1/22
(52) U.S. Cl. .................................. 73/863.86; 73/863.72
(58) Field of Search ......................... 73/863.85, 863.81, 73/863.86, 863.73, 863.72, 863.83

(56) References Cited

U.S. PATENT DOCUMENTS

| 3,681,997 A | * | 8/1972 | Allen et al. ............... 73/863.84 |
| 3,896,673 A | * | 7/1975 | Audouze et al. .......... 73/863.33 |
| 3,950,136 A | * | 4/1976 | Bellinga ................... 73/863.86 |
| 4,173,895 A | * | 11/1979 | Pecor ........................... 73/864 |
| 4,252,021 A | * | 2/1981 | Drushel .................... 73/863.72 |
| 4,380,176 A | * | 4/1983 | Bauer et al. .............. 73/863.86 |
| 4,928,536 A | * | 5/1990 | Welker ...................... 73/863.83 |
| 5,325,731 A | * | 7/1994 | Miller et al. .............. 73/863.86 |
| 5,370,146 A | * | 12/1994 | King et al. ................... 137/8 |
| 6,038,934 A | * | 3/2000 | Peterson ................... 73/863.86 |
| 6,289,752 B1 | * | 9/2001 | Nimberger et al. ....... 73/863.11 |

* cited by examiner

Primary Examiner—Hezron Williams
Assistant Examiner—Nashmiya Fayyaz
(74) Attorney, Agent, or Firm—Browning Bushman

(57) ABSTRACT

A combination purging system and sampling system is provided for sampling gas from a pipeline. A flow path 40 provides fluid communication between a sample bottle 45 and the pipeline. The sample bottle 45 is initially filled with an inert gas for purging air from the flow path 40 and venting to atmosphere. A supply valve 24 controls flow between the pipeline and the flow path 40, and a bleed valve 35 controls venting from the flow path 40 to atmosphere. The relationship and positioning between the valves and the flow path prevents condensation from entering the sampled gas while purging and sampling.

15 Claims, 3 Drawing Sheets

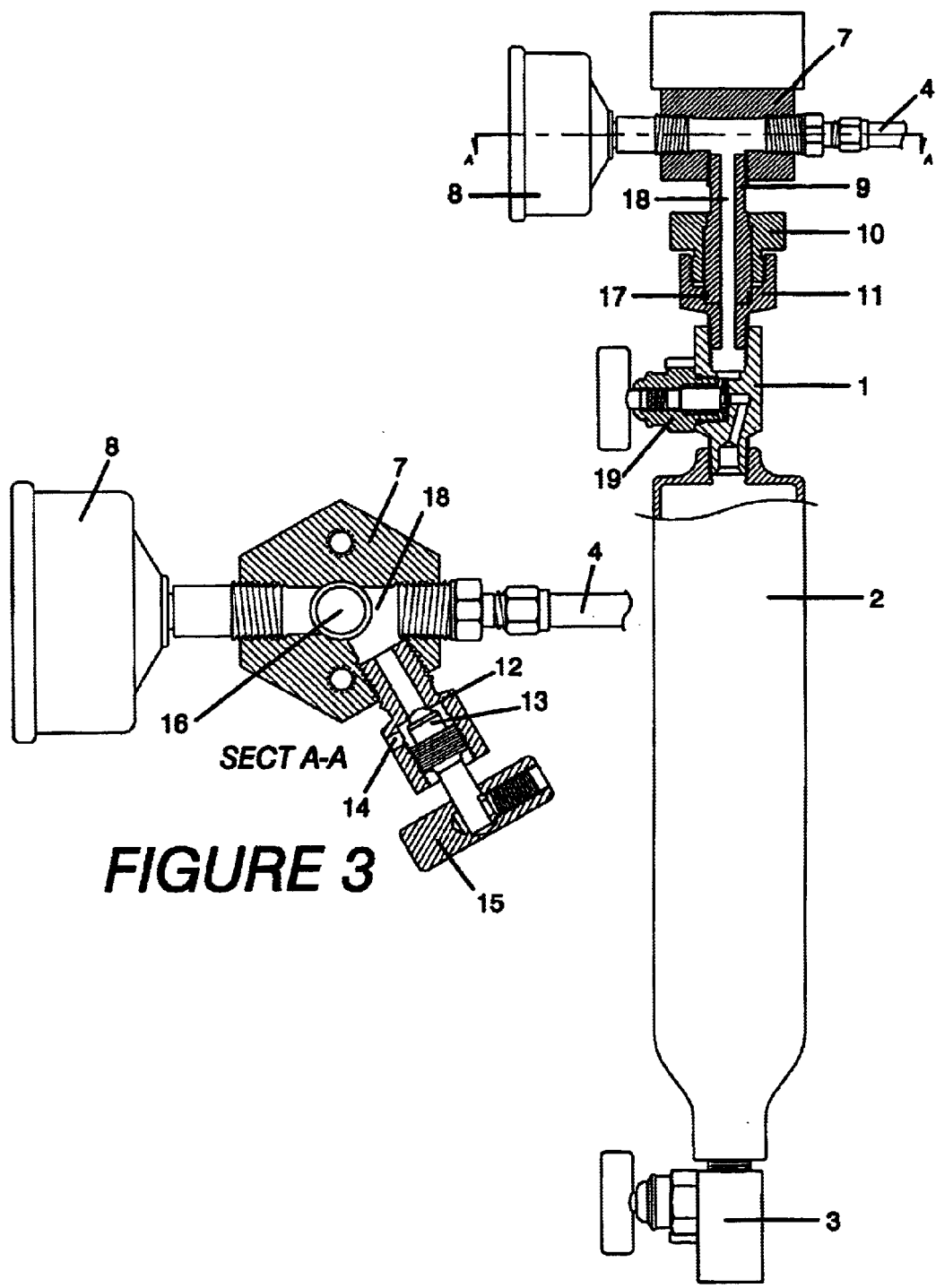

PURGING SYSTEM FOR USE WITH A GAS SAMPLING SYSTEM

This application claims the benefit of Provisional Application No. 60/323,128, filed Sep. 17, 2001.

FIELD OF THE INVENTION

The present invention relates to a purging system in a heated enclosure for housing a sampling system along a gas pipeline. More particularly, the invention relates to a selected gas filled sample bottle and a purge block for use when replacing a sample bottle.

BACKGROUND OF THE INVENTION

FIG. 1 shows a heated enclosure system where many and preferably all the components of a sampling system are heated and maintained at a temperature above the dew point of the hydrocarbon gas being sampled.

When sampling period ends and it is time to collect the filled bottle and replace it with an empty bottle at a given sampling station, an operational problem occurs that has not been resolved by the prior art.

The typical procedure for commissioning an empty bottle at a sampling station is to connect the bottle to the sampling system and then, since the bottle contains air, to perform a purging process to purge air out of the sample line from the pump to the bottle, from the bottle connection, and from the bottle itself. This must be done because air will contaminate the sample and make the BTU analysis inaccurate.

The purging process consisting of several purge cycles is typically performed to purge the sampling system of air. A purge valve 5 on the sample pump is opened to allow sample gas to flow freely in response to pipeline pressure around the pump to the "sample out" line 4. With the purge valve 5 open, the operator performs the first purge cycle. Valve 1 is first opened to pressurize fresh bottle 2 to pipeline pressure. Valve 3 is then closed again, valve 1 is opened, and this purge cycle is repeated, typically about three or more times for higher pipeline pressures, and up to ten times for lower pipeline pressures. Finally, the purge valve is closed, the bottle is bled down to near zero, and outlet valve 3 is closed again to complete the purging process.

With the purging process complete, the operator begins the sampling period during which a number of gas samples are taken from the pipeline and added to the sample bottle. The sampling period generally lasts about a month, during which the accumulated samples may pressurize the bottle to nearly pipeline pressure.

A typical prior art bottle connection system is shown in FIG. 2. Sample out line 4 connects to and supplies gas for gas sampling to distribution block 7, which is fastened to the top inside surface of the heated enclosure as shown in FIG. 1. Gauge 8 is typically found in the system to monitor pressure in the sample line. Male quick connector member 9 is permanently threaded into block 7. Hand operated fastening nut 10 engages the female threads of the bottle quick connection member 11 to attach the bottle assembly to the gas distribution block with O-ring 17 perfecting the seal.

Member 11 is permanently attached to inlet valve 1 as the bottle side component of the hand operated quick connect system. An alternate method of connecting the bottle 2 to the distribution block 7 would be to use a male/male outlet valve 1 and thread valve 1 directly into block 7. This is not preferred due to the continued space and the time involved in making that type of connection. Bleed body 12 which carries bleed stem 13 is typically closed and is opened prior to disconnect by turning handle 15 to allow trapped high pressure gas to vent from cavity 18, allowing hand operated disconnect of the bottle using connection nut 10. With systems of this or similar type, there is no way to purge all the air from cavity 18 after connection of the new sample bottle.

A major problem with prior art is that the purging process artificially increases the percentage of "heavy" rich gas components present in the sample. If the purging process is performed on a bottle that is "cold," i.e., below the dew point of the gas being sampled, some of the heavy components of the gas will condense on the inner walls of the sample bottle during each purging cycle. Because the purging process requires several purging cycles, the sample bottle will become "loaded" with heavy gas components accumulated during each purging cycle. When that bottle is taken to a lab for analysis, it is heated to revaporize any components in the gas that had condensed out of the vapor phase during the trip to the lab, so that when the gas vapor is run through the chromatograph it will contain all of the constituents of the gas in the sample bottle. This heating will revaporize heavy components accumulated during the purging process and cause the gas analysis to be incorrectly high in BTU content.

Another problem with prior art is the need to perform multiple purge cycles to effectively purge the sampling system. This multiplies the number of steps the operator must perform, which, in turn, multiplies the chance of operator error, as well as the time and expense involved in the purging process.

The disadvantages of the prior art are overcome by the present invention, and an improved purging system for use in a heated enclosure housing a sampling system along a gas pipeline is hereinafter disclosed. The invention also includes the use of a new purge block for use when replacing a sample bottle.

SUMMARY OF THE INVENTION

A preferred embodiment of the invention involves the use of a "fresh" sample bottle filled with helium or other selected gas. If a sample bottle contains a low pressure (about 10 psi) charge of helium, a valid gas sample can be taken "on top" of the helium since the helium (unlike air) can be selectively excluded from the sample analysis. In a situation where helium is already present in the gas being sampled, another gas, such as argon, may be used for the same purpose. The gas chosen to fill the fresh sample bottle should not be present in the pipeline, in the gas transmitted through the pipeline so that it can easily be identified in the gas analysis operation.

When the "empty" sample bottle contains helium, there is no need to perform the "fill and empty" air purging process. Even if the bottle is cold when the first several "bites" of gas are placed in the bottle and the heavy components of the gas condenses out on the walls of the bottle, this is permissible since these heavy components "belong" in the bottle of sampled gas and will be revaporized when the bottle is subsequently heated in the lab. When using a helium filled bottle in a heated enclosure, substantially all air between the connection to the sample pump and the inlet valve of the helium filled bottle is removed and replaced with helium during change out of the bottle. A preferred sample block to achieve this objective is disclosed.

It is an object of the present invention to provide a purging system for use with a sampling system along a gas pipeline. The sampling system includes a sample bottle for storing samples of gas from the pipeline, and a pump for passing gas from the pipeline into the sample bottle. The purging system includes a purge block which defines a flow path between the sample bottle and atmosphere. A supply valve is provided along the flow path for controlling the flow between the gas pipeline and the purge block. The sample bottle contains a selected inert gas for purging air from the purge block, and conventionally includes a bottle valve for controlling the flow between the purge block and the sample bottle. A bleed valve is provided along the flow path for vent to atmosphere. When the supply valve is closed, inert gas is passed from the sample bottle through the purge block and vents to atmosphere to purge the flow path prior to passing gas from the pipeline into the sample bottle.

Another object of the invention is to provide an improved method for purging air from a sampling system prior to sampling gas from a gas pipeline, with a sampling system including a sample bottle for storing gas from the pipeline and a pump for passing gas from the pipeline to the sample bottle. A purge block is provided defining a flow path for fluid communication between the pipeline, the sample bottle, and atmosphere. Supply valve, along with flow path is controlled to regulate flow between the gas pipeline and the purge block, while a bottle valve controls flow between the purge block and the sample bottle. A bleed valve is controlled along the flow path for venting to atmosphere. With the supply valve closed, the bottle valve is opened and the bleed valve is opened to pass inert gas from the bottle into the flow path and purge air from the purge block.

It is a feature of the invention that a supply portion of a flow path in the block extends between the pipeline and the supply valve, and a bottle portion of a flow path extends between the supply valve and the bottle valve. The bleed portion of the flow path in the purge block may extend between the supply valve and the bleed valve. In a preferred embodiment, the bottle portion is in fluid communication with the bleed portion regardless of the supply valve position, which may be accomplished by providing a bypass chamber providing fluid communication between the bottle portion and the bleed portion when the supply valve is closed.

It is a further feature of the invention that the bottle portion of a flow path passes above the supply valve, such that fluid condensation above the supply valve cannot pass through the sample bottle.

It is a further feature of the invention that the bleed valve and the bleed portion of the flow path are positioned below the supply valve, such that fluid condensation about the supply valve flows through the bleed portion toward the bleed valve.

Various types of inert gases may be used according to the present invention. A suitable inert gas would be helium and argon for many applications, since neither of these gases is ordinarily present in a gas pipeline, and can thus be easily eliminated by the test equipment.

It is a further feature of the invention that various types of pressure sensors may be provided along the flow path in the sample block to sense pressure in the flow path.

These and further objects, features, and advantages of the present invention will become apparent from the following detailed description, wherein reference is made to the figures in the accompanying drawings.

BRIEF DESCRIPTION OF THE DRAWINGS

FIG. 2 is a prior art pictorial view, partially in cross-section, of the components between the flow line from the sample pump and the sample bottle.

FIG. 3 is a cross-sectional view along lines A—A in FIG. 2.

DETAILED DESCRIPTION OF THE PREFERRED EMBODIMENT

Figure 1:
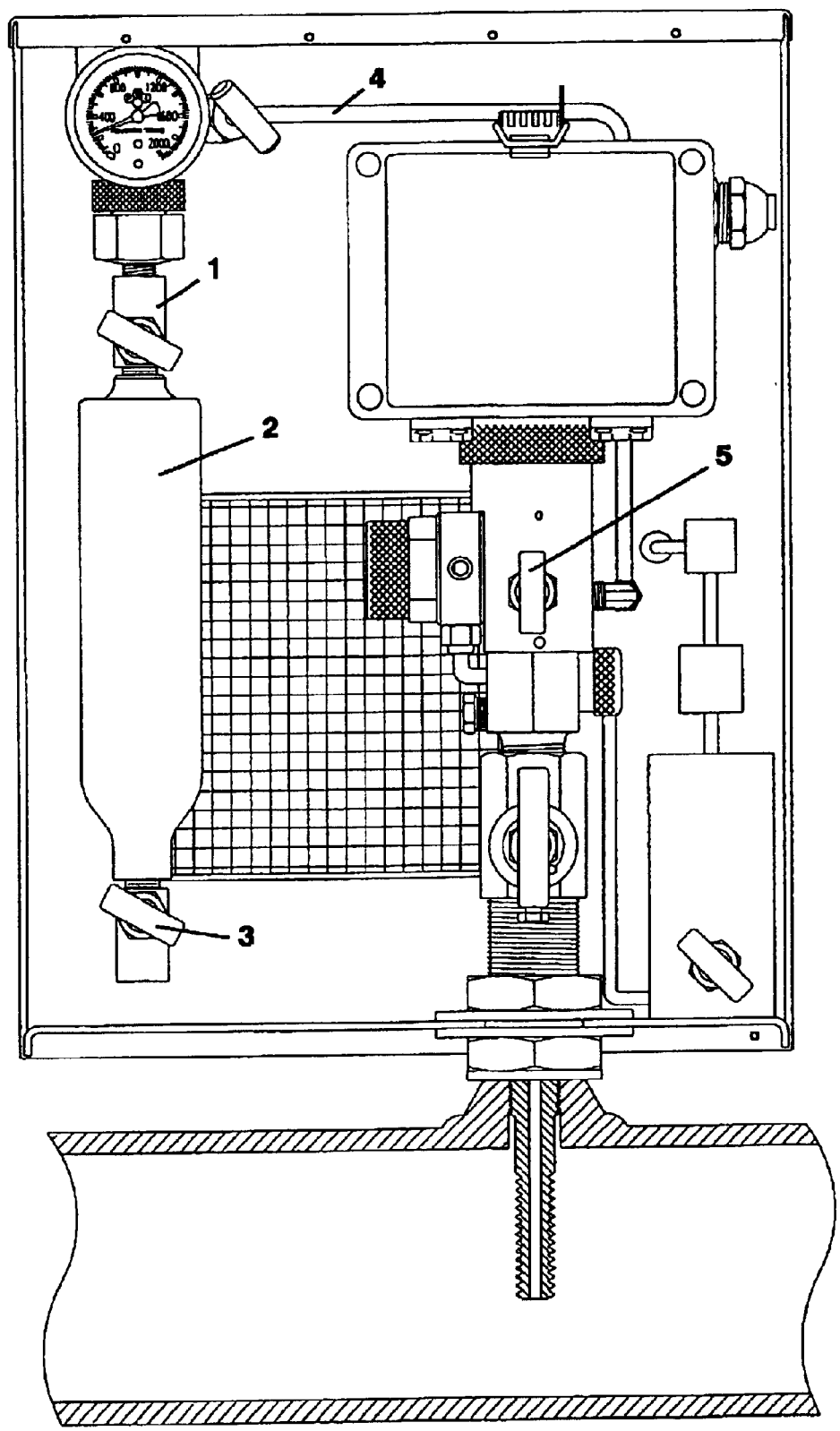
FIG. 1 illustrates a prior art heated enclosure sampling system along a gas pipeline for sampling gas.
Figures 4, 4A:
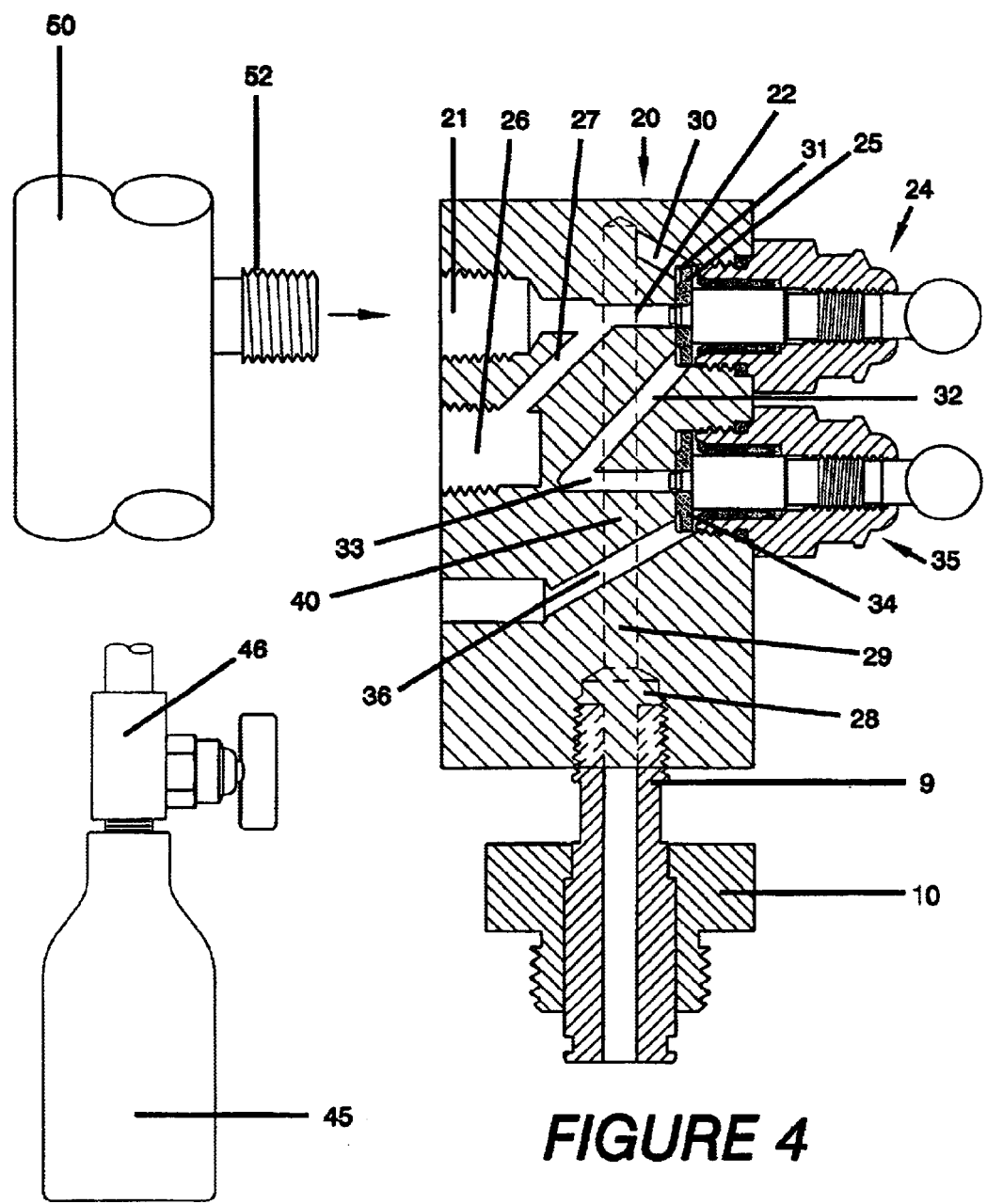
FIG. 4 is a cross-sectional view of a purge block according to the present invention for positioning between the flow line from the pump and a fastening nut for securing a quick connect member to an inlet valve on the sample bottle.
FIG. 4A is a pictorial view of the sample bottle to be used with the sampling and purging system.

FIG. 4 shows a purge block 20 according to the present invention, which replaces the prior art purge block 7 shown in FIG. 2. The purge block 20 defines a flow path 40 which provides fluid communication between a pipeline such as pipeline 50, a sample bottle 45 (as shown in FIG. 4A), and atmosphere. The pipeline 50 is in communication with the flow path 40 via an NPT port 21, such as by threaded connection with male NPT threads 52. A male connector 9 and a fastening nut 10 interconnect the purge block 20 to the sample bottle 45. Gas enters the flow path 40 of the purge block 20 via NPT port 21 and passes to a supply portion 22 of the flow path 40 and to a supply valve 24. Closure of the supply valve 24 before the full sample bottle 45 is removed will trap gas between valve seat 25 and the pipeline 50, and this gas will be free of air.

Sensor port 26 connects to the supply portion 22 to register pressure using a pressure sensor, e.g., with gauge 8, via conduit 27, and will stay filled with gas with supply valve 24 closed. When the full sample bottle 45 is removed, air will enter a bottle portion 29 of the flow path 40 where connector member 9 threadingly connects to bottle port 28 of purge block 20. The air will infiltrate the bottle portion 29 which extends to a circular bypass chamber 31 adjacent valve seat 25. Air will continue to infiltrate through the bypass chamber 31 around valve seat 25 to passageways 32 and 33, and then be blocked by a seat 34 of a closed bleed valve 35. Passageways 32 and 33 are segments of a bleed portion 42 of the flow path 40 between the supply valve 24 and the purge valve 35.

When a fresh sample bottle 45 that contains a positive pressure of helium is connected to the system as shown in FIG. 4, the air present in the flow path 40 of purge block 20, as described above, must be eliminated before sampling can begin, in order to obtain an accurate sample. That is accomplished by opening a bottle valve 46 of the fresh helium filled sample bottle 45, which will introduce pressure from the helium filled sample bottle 45 all throughout the flow path 40 along the bottle portion 29, through the bypass chamber 31, along the bleed portion 42, and to the closed seat 34 of bleed valve 35. Bleed valve 35 is then cracked open to flush all the air from these passageways, replacing the air with helium. Bleed valve 35 is closed again, preferably before all of the helium pressure in sample bottle 45 is exhausted. Valve 46 on the bottle is then closed since the typically high pressure gas trapped in the supply portion 22 under seat 25 from the previous sampling period must be bled to near zero before the bottle valve 46 is opened, so that sample bottle 45 does not become partially pressurized with the gas in the supply portion 22 of the flow path 40. Supply valve 24 is then opened fully, bleed valve 35 is cracked open and gas pressure that was trapped in NPT port 21 is bled down to near zero. The sampling period is started with the bottle pressure near zero, and by the end of the sampling period, the bottle pressure has typically risen to nearly pipeline pressure.

In the above step, opening supply valve 24 prior to bleed valve 35 is important. At the end of the previous sampling period, the supply portion 22 of the flow path 40 is at or near pipeline pressure, typically over 500 psi and often up to 1000 psi. When that pressure is bled down to near zero so that the new cycle can start, a Joules Thompson effect will occur at the valve being opened, which will cool the immediate area and cause liquids to precipitate out of the gas phase. Any precipitation of the hydrocarbon gas desirably occurs in a vent passageway 36 so that those components are expelled from the system, rather than being condensed out in passageways 32 and 33, of the bleed portion 42 to be later revaporized during the course of the sampling period by the enclosure heating, and erroneously reentering the sampled gas being placed in the sample bottle 45. For the same reason, the vent passageway 36 is located on the low side of the purge valve so that precipitated liquids will be expelled.

Bleed valve 35 is desirably below supply valve 24 so that passageway 32 can be positioned on the low side of valve seat 25. When supply valve 24 is opened to the high pressure in the supply portion 22, the passageways leading to those respective valve seats will become pressurized, even though valves 46 and 35 are closed, and it is possible that a small amount of liquid will drop out at seat 25 when the supply valve 24 is opened. If any liquid is present in bypass chamber 31 or in the flow path 40 about the supply valve 24, as a result of opening valve 24, it may be expelled through passageways 32 and 33 when bleed valve 35 is throttled open to bleed the supply portion 22 down to near zero. For the same reason, a passageway 30 of the bottle portion 29 is preferably positioned high (vertically above) bypass chamber 31 so that any precipitated liquid will not flow into passageway 30.

It is a feature of the present invention that a unitary and homogenous material sample block be provided for mounting valves which serve the function of valves 24 and 25, with the various gas inlet, gas outlet, and connecting passageways being provided within the sample block for performing the above operations. Positioning of the various passageways and components as discussed above is thus preferred to minimize the likelihood of any hydrocarbon gas precipitating out during bottle change over and incorrectly becoming part of the mixture in the bottle which is subsequently sampled.

The term "inert gas" as used herein refers to any gas which is not present in the gas pipeline, or may otherwise be excluded during subsequent analysis of the sample gas. The term "pressure sensor" as used herein refers to any device for sensing and indicating pressure, such as an analog pressure gage or electronic sensor. A purge block according to the present invention is preferably a unitary metal block on which the purge valve and the bleed valve are mounted. In other embodiments, a purge block could comprise two adjacent or spaced blocks, and both the supply valve and the bleed valve could be mounted at a location other than the purge block to perform their desired function. In a preferred embodiment, the bleed valve along the flow path controls the venting of gas in the flow path to atmosphere. In an alternate embodiment, various types of gas storage devices could be provided downstream from the bleed valve, so that the bleed valve vented gas from the flow path, but not necessarily to atmosphere.

The problem of heavy rich loading of the sample bottle during the fill and empty process could theoretically be alleviated by placing a fresh bottle in the heated enclosure and waiting for several hours for the bottle to be heated up to temperature before the "fill and empty" cycle was begun. This is not considered a practical solution since it would require a significant increase in the sample collection crew size since the time spent at each station to collect a sample would be increased tremendously.

A more practical although expensive solution is to leave an extra empty bottle inside the heating cabinet so that when a full bottle is removed, a preheated bottle is available so the "fill and empty" process can be done immediately. This solution requires that the fleet of sample bottles be increased by one-third since three bottles per sample station could be required rather than two as in the past (one being filled, one at the lab and then cleaned for the next use).

Another solution could be heating the bottles by some means on the field truck used to travel to the various sample sites and then somehow get the bottle from the truck to the sample site, without letting its temperature drop below the dew point. This solution is considered difficult to implement and is too easily bypassed or compromised by the field technician for the sake of operational expediency.

It will be understood by those skilled in the art that the embodiment shown and described is exemplary and various other modifications may be made in the practice of the invention. Accordingly, the scope of the invention should be understood to include such modifications which are within the spirit of the invention.

What is claimed is:

1. A purging system used in conjunction with a sampling system along a gas pipeline, the sampling system including a sample bottle for storing samples of gas from the pipeline, the purging system comprising:

a purge block defining a flow path for fluid communication between the pipeline, the sample bottle, and atmosphere, the purge block being a unitarian homogeneous material block;

a supply valve supported on the purge block and positioned along the flow path for controlling flow between the gas pipeline, the sample bottle and a bleed valve;

a bottle valve for controlling flow between the purge block and the sample bottle;

the bleed valve supported on the purge block and positioned along the flow path for venting to atmosphere;

the bleed valve and a bleed portion of the flow path are positioned below the supply valve, such that fluid condensation about the supply valve flows through the bleed portion toward the bleed valve; and;

the sample bottle containing a selected inert gas for purging air from the purge block and subsequently receiving the samples of gas from the pipeline.

2. A purging system as defined in claim 1, wherein a supply portion of the flow path extends from a supply inlet port in the purge block to the supply valve, a bottle portion of the flow path separate from the supply portion extends from a bottle inlet port in the purge block to the supply valve, and the bleed portion of the flow path separate from the supply portion and the bottle portion extends between the supply valve to the bleed valve.

3. A purging system as defined in claim 2, wherein the bottle portion is in fluid communication with the bleed valve when the supply valve is closed.

4. A purging system as defined in claim 3, further comprising:

a bypass chamber about a valve seat for the supply valve providing fluid communication between the bottle portion and the bleed valve with the supply valve closed.

5. A purging system as defined in claim 4, wherein the bypass chamber is an annular chamber surrounding the valve seat for the supply valve.

6. A purging system as defined in claim 1, wherein a bottle portion of the flow path passes above the supply valve, such that fluid condensation about the supply valve cannot pass to the sample bottle.

7. A purging system as defined in claim 1, wherein the inert gas is selected from the group consisting of helium and argon.

8. A purging system as defined in claim 1, further comprising:

a pressure sensor along the flow path for sensing the pressure in the flow path.

9. A purging system as defined in claim 2, wherein each of the supply valve and the bleed valve extend from a face of the purge block opposite the supply inlet port, for passing gas from the pipeline into the purge block.

10. A method of purging air from a sampling system prior to sampling gas from a gas pipeline, the sampling system including a sample bottle with a bottle valve the sample bottle for storing gas from the pipeline, the method comprising:

providing a flow path for fluid communication between the pipeline, the sample bottle, and atmosphere;

positioning a supply valve along the flow path for controlling flow between the gas pipeline, the sample bottle and a bleed valve;

positioning the bleed valve along the flow path for venting gas from the flow path; positioning the bleed valve and a bleed portion of the flow path below the supply valve, such that fluid condensation about the supply valve flows through the bleed portion toward the bleed valve;

filling the sample bottle with a selected inert gas;

attaching the sample bottle along the flow path;

closing the supply valve, opening the bottle valve, and opening the bleed valve to purge air from the sampling system; and closing the bleed valve and opening the supply valve to pass sampling gas from the pipeline to the sample bottle.

11. A method as defined in claim 10, further comprising:

providing a bypass chamber for fluid communication between the bottle valve and bleed valve regardless of the position of the supply valve.

12. A method as defined in claim 10, further comprising:

closing the bottle valve, some inert gas remaining in the sample bottle.

13. A method as defined in claim 10, further comprising:

passing a bottle portion of the flow path above the supply valve, such that fluid condensation about the supply valve cannot pass to the sample bottle.

14. A method as defined in claim 10, further comprising:

positioning the bleed valve and a bleed portion of the flow path below the supply valve, such that fluid condensation about the supply valve flows through the bleed portion toward the bleed valve.

15. A method as defined in claim 14, further comprising:

after filling the sample bottle and before beginning a new filling cycle, reducing the pressure in a supply portion of the flow path by opening the supply valve, then opening the bleed valve, such that any condensation resulting from a rapid reduction in pressure in the flow path occurs about the bleed valve, whereupon the condensation will flow through the bleed valve to atmosphere.

* * * * *

UNITED STATES PATENT AND TRADEMARK OFFICE
CERTIFICATE OF CORRECTION

PATENT NO. : 6,854,346 B2
DATED : February 15, 2005
INVENTOR(S) : Spence M. Nimberger It is certified that error appears in the above-identified patent and that said Letters Patent is hereby corrected as shown below:

Column 6,
Line 48, change "and;" to -- and --.

Column 7,
Line 21, change "valve" to -- valve, --.

Signed and Sealed this

Third Day of May, 2005

JON W. DUDAS
*Director of the United States Patent and Trademark Office*